(12) United States Patent
Bettenga

(10) Patent No.: US 11,051,803 B2
(45) Date of Patent: Jul. 6, 2021

(54) SUTURE/NEEDLE CONSTRUCTS AND METHODS OF MANUFACTURE THEREOF

(71) Applicant: Smith & Nephew, Inc., Memphis, TN (US)

(72) Inventor: Mason Bettenga, Memphis, TN (US)

(73) Assignee: Smith & Nephew, Inc., Memphis, TN (US)

(*) Notice: Subject to any disclaimer, the term of this patent is extended or adjusted under 35 U.S.C. 154(b) by 127 days.

(21) Appl. No.: 16/170,258

(22) Filed: Oct. 25, 2018

(65) Prior Publication Data

US 2019/0125340 A1 May 2, 2019

Related U.S. Application Data

(60) Provisional application No. 62/577,488, filed on Oct. 26, 2017.

(51) Int. Cl.
| | |
|---|---|
| *A61B 17/06* | (2006.01) |
| *A61B 17/00* | (2006.01) |
| *A61F 2/08* | (2006.01) |
| *A61B 17/04* | (2006.01) |

(52) U.S. Cl.
CPC .. *A61B 17/06166* (2013.01); *A61B 17/06066* (2013.01); *A61B 2017/00526* (2013.01); *A61B 2017/00884* (2013.01); *A61B 2017/00893* (2013.01); *A61B 2017/0477* (2013.01); *A61F 2/08* (2013.01)

(58) Field of Classification Search
CPC ............ A61B 17/0401; A61B 17/0469; A61B 17/06166; A61B 17/00526; A61B 17/00884; A61B 17/0477; A61B 2017/0464; A61B 2017/047; A61B 2017/0472; A61B 2017/06052; A61B 2017/06057; A61B 2017/06185; A61B 2017/061; A61F 2/0811; A61F 2002/0852
See application file for complete search history.

(56) References Cited

U.S. PATENT DOCUMENTS

| | | | | |
|---|---|---|---|---|
| 2007/0135843 | A1* | 6/2007 | Burkhart | A61B 17/06166 606/232 |
| 2010/0040662 | A1* | 2/2010 | Cotton | A61L 31/048 424/423 |
| 2010/0160962 | A1* | 6/2010 | Dreyfuss | A61F 2/0811 606/228 |
| 2011/0208239 | A1* | 8/2011 | Stone | A61B 17/0469 606/228 |
| 2012/0245629 | A1* | 9/2012 | Gross | A61B 17/06166 606/228 |

* cited by examiner

*Primary Examiner* — Katrina M Stransky
*Assistant Examiner* — Mohammed S Adam
(74) *Attorney, Agent, or Firm* — Burns & Levinson, LLP; Joseph M. Maraia

(57) ABSTRACT

Suture/needle constructs are disclosed in which either a first round or flat section of suture can be crimped on a needle. If the first section is round, then a transition to flat second section is formed by a braiding machine. After a short space of flat, the braiding machine weaves a bifurcation into the second section, forming third and fourth suture sections. The third and fourth suture sections transition back together again into a woven fifth section at a distance from the needle, which forms a suture loop. This looped section of the suture can then be used for whipstitching a tendon or a ligament graft.

20 Claims, 1 Drawing Sheet

SUTURE/NEEDLE CONSTRUCTS AND METHODS OF MANUFACTURE THEREOF

CROSS-REFERENCE TO RELATED APPLICATIONS

This application claims priority to and benefit of U.S. Provisional Application No. 62/577,488, filed Oct. 26, 2017, entitled SUTURE/NEEDLE CONSTRUCTS AND METHODS OF MANUFACTURE THEREOF, the contents of which are incorporated by reference herein in their entirety for all purposes.

FIELD

The present disclosure relates to suture/needle constructs for repairing soft tissue and, in particular, suture/needle constructs for whipstitching a soft tissue graft, such as tendon graft.

BACKGROUND

A ligament is a piece of fibrous tissue which connects one bone to another within the body. Ligaments are frequently damaged (e.g., detached, torn or ruptured) as the result of injury or accident. A damaged ligament can impede proper stability and motion of a joint and cause significant pain. The damaged ligament can be replaced or repaired using various procedures, a choice of which can depend on a particular ligament to be restored and on the extent of the damage. When ligaments are damaged, surgical reconstruction can be necessary, as the ligaments may not regenerate on their own.

An example of a ligament that is frequently damaged as a result of injury, overexertion, aging and/or accident is the anterior cruciate ligament (ACL) that extends between a top of the tibia and a bottom of the femur. ACL repair typically includes the use of a ligament graft replacement procedure which usually involves drilling a bone tunnel through the tibia and up into the femur. A ligament graft, which may be an artificial ligament or harvested graft, such as a tendon, is then passed through a tibial portion of the tunnel across the interior of the joint, and up into a femoral portion of a tunnel. One end of the ligament graft can then be secured in the femoral tunnel and another end of the graft is secured in the tibial tunnel, at the sites where the natural ligament attaches.

A common ACL ligament reconstruction procedure involves using an autograft, which is a portion of the patient's own tendon that would replace the damaged natural ligament. The autograft is often a hamstring tendon, though other tendons can be used (e.g., a patellar tendon). The ligament graft can also be obtained from a donor ("allograft"). In these procedures, a suture/needle construct is used to put stitches or sutures in the graft and prepare the stitched or sutured graft for fixation within the bone tunnel. Currently-available products, however, are typically limited to homogeneous round sutures made into a loop. Accordingly, improved suture/needle constructs that allow for maximum suture fixation strength and accelerated tissue healing are needed.

SUMMARY

Disclosed herein is a suture/needle construct in which either a first round or flat section of suture can be crimped on a needle. If the first section is round, then a transition to flat second section is formed by a braiding machine. After a short space of flat, the braiding machine weaves a bifurcation into the second section, forming third and fourth suture sections. The third and fourth suture sections transition back together again into a woven fifth section at a distance from the needle, which forms a suture loop. This looped section of the suture can then be used for whipstitching a tendon or a ligament graft. If desired by the user, the suture can also be bifurcated a second time by the braiding machine, creating either a second loop or tails for additional fixation points.

Further examples of the suture/needle constructs of this disclosure may include one or more of the following, in any suitable combination.

In examples, the suture/needle construct of this disclosure includes a length of suture having a first section and a second section extending along the length of suture. A needle is attached to the first section. A first bifurcation in the second section defines a third section and a fourth section extending along the length of suture. A fifth section is defined by a weaving together of the third section and the fourth section. The second section, the third section, the fourth section and the fifth section define a first suture loop. In examples, a cross-section of the first section is substantially round. In other examples, a shape of the first section is substantially, flat. In examples, a shape of the second section, the third section, the fourth section and the fifth section is substantially flat.

In other examples, the suture/needle construct further includes a second bifurcation in the fifth section of the length of suture. In examples, the second bifurcation defines suture tails. In other examples, the second bifurcation defines a sixth section and a seventh section extending along the length of suture. In examples, a shape of the suture tails is substantially flat. In other examples, a shape of the suture tails transitions from a substantially flat portion to a substantially round portion. In examples, the suture/needle construct further includes an eighth section defined by a weaving together of the sixth section and the seventh section. The fifth section, the sixth section, the seventh section, and the eighth section define a second suture loop. A shape of the fifth section, the sixth section, the seventh section and the eighth section is flat. In examples, the suture/needle construct further includes a third bifurcation in the eighth section of the length of suture, the third bifurcation defining suture tails.

In further examples, the suture/needle construct of this disclosure is at least partially formed by a braiding machine. In examples, the needle is an eyeless needle. In examples, the first and second suture loops are fixed loops. In examples, the length of suture comprises a biologically active material. In other examples, the graft is a tendon graft.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1:
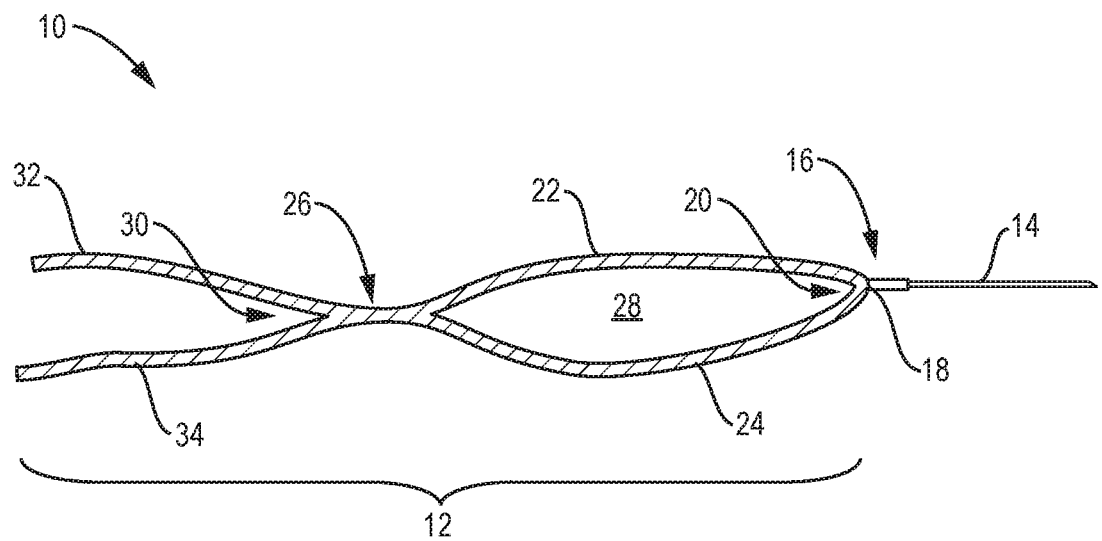
FIG. 1 illustrates a first example of a suture/needle construct of this disclosure having one looped section.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the disclosure, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Referring now to FIG. 1, an exemplary suture/needle construct 10 of this disclosure is shown. The suture/needle construct 10 can be used to whipstitch or other multi-stitch soft tissue, such as a tendon graft. However, it may be appreciated that the suture/needle construct 10 of this disclosure can be used in other orthopedic surgical operations.

As shown in FIG. 1, the suture/needle construct 10 generally comprises a length of suture 12 having at least one suture loop 28, and a needle 14. The material or filaments forming the suture 12 may be made of any one of usual suture materials, such as silk, cotton, polyethylene, or nylon, presently used for making sutures. Additionally, the suture 12 may be comprised of a biologically active material. The biologically active material may be comprised of a water soluble or water miscible angiogenic material or precursor thereof in admixture with a non-absorbable hydrophobic polymer. For example, the biologically active material may be an angiogenic material as described in U.S. Pat. No. 8,541,027 and U.S. Publication No. 2010/0040662, the disclosures of which are incorporated by reference herein in their entirety. The angiogenic material so described may advantageously stimulate tissue repair in the area surrounding the ACL tear and release factors that promote angiogenesis. The suture 12 may be impregnated (e.g., dipped or soaked) with the biologically active material after manufacture of the suture 12, such that the biologically active material is distributed throughout up to the whole of the suture 12. Alternatively, the biologically active material may be physically incorporated into the main fabric of the suture 12. For example, threads of biologically active material may be braided with polyethylene terephthalate fibers used to produce the suture 12. The biologically active material may be present in an amount that is therapeutically effective for humans.

In examples, the length of suture 12 is manufactured using standard commercial braiding machinery without interrupting the linear continuity of the suture 12. For example, the length of suture 12 described herein can be manufactured using a Shima Seiki SWG 041N machine, a Herzog LZ2 series machine, a Herzog NG2 series machine, a Comez DNB-800 machine for narrow nets, a Double Bar Raschel machine HDR8, or a Karl Mayer Double needle bed warp knitting machine. The braiding machine may be equipped with multiple spools of yarn that are each loaded on one of multiple carriers of the braiding machine. The yarn may be formed from twisted together monofilament fibers or air-entangled monofilament fibers, where the particular monofilaments used to form a particular yarn may be dependent upon the application. For example, yarns used to form the length of suture 12 may comprise monofilament fibers, where the yarns have a minimum denier of 198, to a maximum denier of 792. A braiding machine having at least 8 carriers, and up to 16 carriers, may be used to form the suture 12, where each carrier is equipped with at least one yarn. In some instances, multiple yarns may be loaded on a single carrier of a braiding machine to achieve a desired result. For example, a braiding machine having 12 carriers may be equipped with two yarns per carrier to achieve a desired braid strength or density, such as a braid having a linear mass density of 375 denier. Other configurations may be used depending upon the particular application or the capabilities of a particular braiding machine.

The needle 14 is preferably an eyeless needle in which the length of suture 12 is inserted into an axial opening formed in a blunt end of the needle 14. Advantageously, an eyeless needle does not require threading before or during an operation and will not unthread during use. In examples, the needle 14 is a thin, metal needle (preferably nitinol or stainless steel) that allows an increased number of suture loop passed through or around the tissue to be sutured or attached, with decreased trauma. The needle 14 need not be straight and may have various shapes or configurations (for example, curved, or a combination of straight and curved), depending on the characteristics of the surgical procedure involved.

In examples, the method of forming the suture/needle construct 10 of FIG. 1 includes using a braiding machine to form a first section 16 of the suture 12. The first section 16 may be either round or flat. The needle 14 is attached, for example, by crimping, to the first section 16 of the suture 12. If the first section 16 is round, the braiding machine will transition the first section 16 to a second section 18, which is flat. After forming the second section 18, the braiding machine will weave at least a first bifurcation 20 into the second section 18. The first bifurcation 20 defines a third section 22 and a fourth section 24 of the suture 12, both of which are flat. In examples, the third section 22 and the fourth section 24 have similar dimensions, including a similar length and width, although dissimilar widths are contemplated by this disclosure. The braiding machine then weaves the third section 22 and the fourth section 24 of the suture 12 back together again, forming a fifth section 26. The fifth section 26 of the suture 12 is also flat and closes the first suture loop 28. As such, the first suture loop 28 is a non-adjustable loop. In further examples, also shown in FIG. 1, a second bifurcation 30 can be woven into the suture 12 to create flat suture tails 32, 34 for additional fixation points. In examples, the tails 32, 34 can be transitioned back to a round cross-section if needed.

Figure 2:
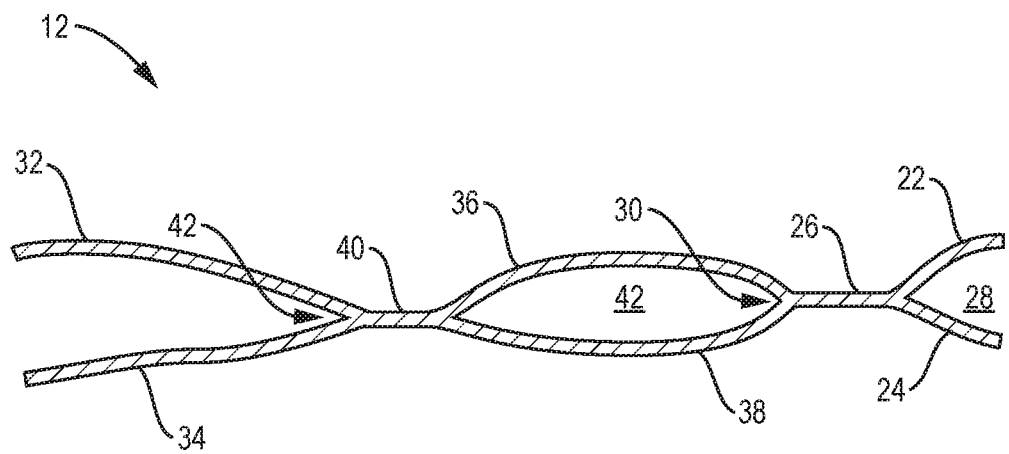
FIG. 2 illustrates a second example of a suture/needle construct of this disclosure having two looped sections.

In another example of the suture/needle construct, shown in FIG. 2, instead of creating suture tails, the second bifurcation 30 may define a sixth section 36 and a seventh section 38 of the suture 12, both of which are flat. In examples, the sixth section 36 and the seventh section 38 have similar dimensions, including a similar length and width, although dissimilar widths are contemplated by this disclosure. The braiding machine then weaves the sixth section 36 and the seventh section 38 of the suture 12 back together again, forming an eighth section 40. The eighth section 40 of the suture 12 is also flat and closes the second suture loop 42. As such, the second suture loop 42 is a non-adjustable loop. In further examples, also shown in FIG. 2, a third bifurcation 42 can be woven into the suture 12 to create either one or more additional suture loops (not shown), or flat suture tails 32, 34 for additional fixation points. In examples, the tails 32, 34 can be transitioned back to a round cross-section if needed.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. A suture/needle construct for stitching a graft comprising:
   a length of suture comprising a first section having a length extending along a central axis, a needle fixedly attached to a terminus of the first section;
   a second section extending from the first section and spaced apart from the needle by the length of the first section, the second section including a first bifurcation defining a third section and a fourth section extending along opposing sides of the central axis; and
   a fifth section defined by a weaving together of the third section and the fourth section, the fifth section having a length extending along the central axis;
   wherein the second section, the third section, the fourth section and the fifth section define a first suture loop.

2. The suture/needle construct of claim 1, wherein a cross-section of the first section is round.

3. The suture/needle construct of claim 1, wherein a shape of the first section is flat.

4. The suture/needle construct of claim 1, wherein a shape of the second section, the third section, the fourth section and the fifth section is flat.

5. The suture/needle construct of claim 1, further comprising a second bifurcation in the fifth section of the length of suture, the second bifurcation being spaced apart from the first suture loop by the length of the fifth section.

6. The suture/needle construct of claim 5, wherein the second bifurcation defines suture tails.

7. The suture/needle construct of claim 6, wherein a shape of the suture tails is flat.

8. The suture/needle construct of claim 6, wherein a shape of the suture tails transitions from a flat portion to a round portion.

9. The suture/needle construct of claim 5, wherein the second bifurcation defines a sixth section and a seventh section extending along opposing sides of the central axis.

10. The suture/needle construct of claim 9, further comprising an eighth section defined by a weaving together of the sixth section and the seventh section, the eighth section having a length extending along the central axis; and wherein the fifth section, the sixth section, the seventh section, and the eighth section define a second suture loop.

11. The suture/needle construct of claim 10, wherein a shape of the fifth section, the sixth section, the seventh section and the eighth section is flat.

12. The suture/needle construct of claim 10, further comprising a third bifurcation in the eighth section of the length of suture, the third bifurcation being spaced apart from the second suture loop by the length of the eighth section, the third bifurcation defining suture tails.

13. The suture/needle construct of claim 12, wherein a shape of the suture tails is flat.

14. The suture/needle construct of claim 12, wherein a shape of the suture tails transitions from a flat portion to a round portion.

15. The suture/needle construct of claim 10, wherein the second suture loop is a fixed loop.

16. The suture/needle construct of claim 1, wherein the suture/needle construct is at least partially formed by a braiding machine.

17. The suture/needle construct of claim 1, wherein the needle is an eyeless needle.

18. The suture/needle construct of claim 1, wherein the first suture loop is a fixed loop.

19. The suture/needle construct of claim 1, wherein the length of suture comprises a biologically active material.

20. The suture/needle construct of claim 1, wherein the graft is a tendon graft.

* * * * *